(12) United States Patent
Knappe et al.

(10) Patent No.: US 7,909,640 B2
(45) Date of Patent: Mar. 22, 2011

(54) CONSOLE WITH A STORAGE SPACE

(75) Inventors: Stefan Knappe, Burghaun (DE);
Juergen Schlitt, Niederaula (DE)

(73) Assignee: Ondal Holding GmbH, Hunfeld (DE)

( * ) Notice: Subject to any disclaimer, the term of this patent is extended or adjusted under 35 U.S.C. 154(b) by 0 days.

(21) Appl. No.: 12/467,773

(22) Filed: May 18, 2009

(65) Prior Publication Data

US 2009/0230064 A1   Sep. 17, 2009

Related U.S. Application Data

(63) Continuation of application No. 11/599,116, filed on Nov. 14, 2006, now Pat. No. 7,566,239.

(30) Foreign Application Priority Data

Nov. 14, 2005 (EP) .................................. 05024778

(51) Int. Cl.
*H01R 11/00* (2006.01)
(52) U.S. Cl. ......................................................... 439/501
(58) Field of Classification Search .................. 439/501,
439/130; 211/26; 108/50.02; 248/222; 280/79.2
See application file for complete search history.

(56) References Cited

U.S. PATENT DOCUMENTS

| | | | |
|---|---|---|---|
| 3,476,344 A | 11/1969 | Pace | |
| 3,769,502 A | 10/1973 | Schultz et al. | |
| 4,132,178 A * | 1/1979 | Mueller et al. | 108/147.14 |
| 4,237,798 A * | 12/1980 | Welsch et al. | 108/192 |
| 4,381,715 A * | 5/1983 | Forman | 108/152 |
| 4,535,175 A | 8/1985 | Squire | |
| 4,535,703 A * | 8/1985 | Henriott et al. | 108/50.02 |
| 4,838,175 A * | 6/1989 | Hauville | 108/25 |
| 4,998,023 A | 3/1991 | Kitts | |
| 5,002,247 A * | 3/1991 | Dispenza et al. | 248/188 |
| 5,237,935 A | 8/1993 | Newhouse et al. | |
| 5,595,428 A | 1/1997 | Huang | |
| 5,881,500 A | 3/1999 | Latino et al. | |
| 5,934,636 A | 8/1999 | Cyrell | |
| 6,254,206 B1 | 7/2001 | Petrick et al. | |
| 6,435,106 B2 * | 8/2002 | Funk et al. | 108/50.02 |
| 6,467,797 B1 | 10/2002 | Lofy et al. | |
| 6,675,722 B2 * | 1/2004 | Stathis et al. | 108/50.02 |
| 6,679,722 B1 * | 1/2004 | Pulizzi | 439/451 |
| 2006/0102054 A1* | 5/2006 | Warriner | 108/50.02 |

* cited by examiner

*Primary Examiner* — Alexander Gilman
(74) *Attorney, Agent, or Firm* — Seed IP Law Group PLLC

(57) ABSTRACT

A console (1), particularly for the hospital sector, with a support device having, in particular, two vertical support tubes (2), has an assembly device (25), which is used to mount at least one tray (5) to the support device. The tray (5) has an upper wall (15) and a lower wall (16). There is at least one storage space (17) between the walls (15,16), and the storage space (17) is provided to accommodate electric cable (18), preferably along with a power plug (19), or another line. In this manner, interfering sections of cable or lines are avoided in the work area.

14 Claims, 3 Drawing Sheets

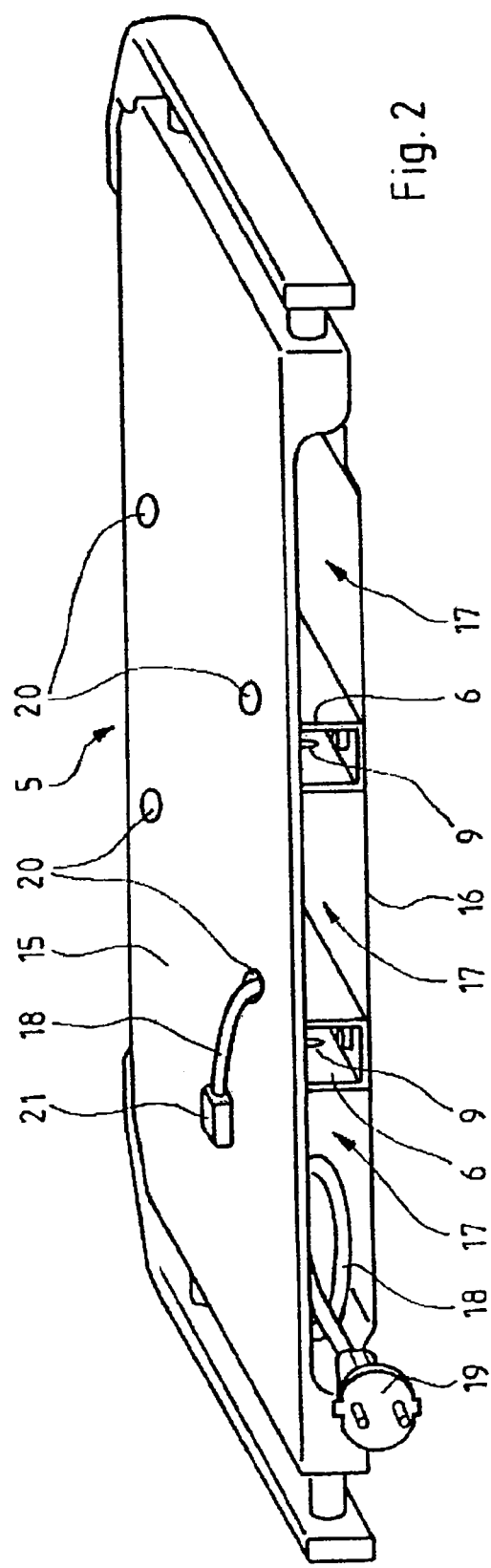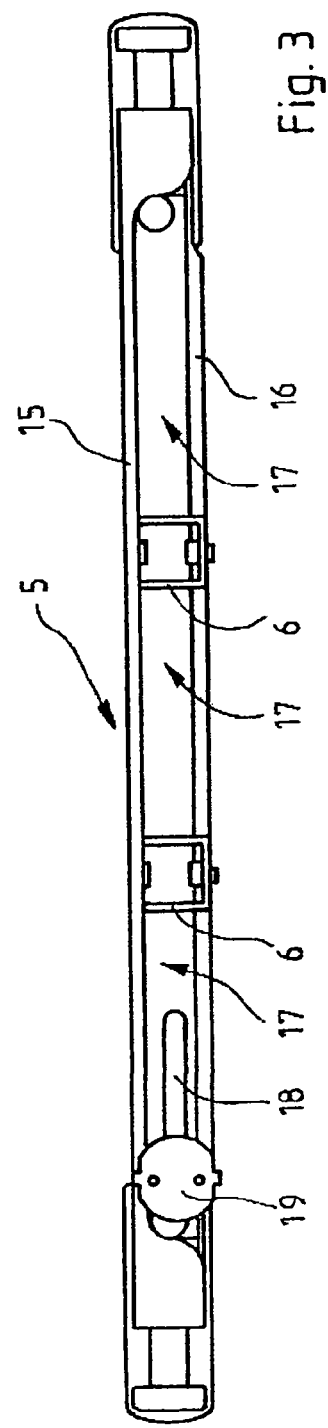

CONSOLE WITH A STORAGE SPACE

CROSS-REFERENCE TO RELATED APPLICATION

This application is a continuation of U.S. patent application Ser. No. 11/599,116, filed Nov. 14, 2006, now pending, which application is incorporated herein by reference in its entirety.

The use of consoles with trays to carry medical devices is known in the hospital sector. In doing so, the devices are arranged on the trays. The electrical connection lines for the devices are routed via the trays, and the connectors for the connection line are plugged into sockets. This is done with gas lines in a similar fashion. The trays have a simple construction and are either inserted at a certain, predetermined height using a plug system or are fixed into place at a certain height using a relatively complicated assembly device.

The known consoles have the disadvantage that the cable and/or lines are sometimes too long, and the excess cable or line lengths can get in the way of persons or even be a tripping hazard.

Thus, the object of the present invention is to provide a solution for this disadvantage.

The console has an assembly device, to which at least one tray on a support device is mounted. The tray has an upper wall and a lower wall. There is at least one storage space between the walls, and the storage space is provided to accommodate electric cable, preferably along with a power plug, or another cable, and/or a supply line.

The proposed innovation has the advantage that some sort of line or cable can be at least partially housed within a tray, because the tray has an upper wall and a lower wall, and the receptacles are provided between the two walls. The areas between the walls are used as storage space. This type of storage space is used to accommodate a cable or any type of supply line (gas, water). This ensures that the lines can be safely stored with respect to their excess length. Tripping hazards due to cable or cable loops are thus avoided.

Advantageous embodiments of the proposed invention are:

If at least one recess is provided in the upper wall, bordering a storage space, for routing electric cable either having a connector socket or to be subsequently provided with a connector socket or other cable (or lines), then a cable which is routed through a storage space (including a water supply or gas supply in addition to an electric cable), can supply a device located on the tray. Only the part of the cable extending from the recess to the device can be seen on the tray. Multiple recesses are used to route multiple cables, data lines, or the like.

If a body is provided on the console, and the body has multiple outlets or supplies for gas or water, which are supplied with electrical current, gas, or water via a supply line, the cable that is in the storage spaces can be supplied a short distance away from a tray, without excessively long cable lines interfering. The supply line is preferably routed from the top down to the console. This is particularly advantageous because, in a preferred embodiment, the support tubes should hang on a ceiling mount. The console could also be used in a hair salon and only be arranged for electric supply.

If two vertical support tubes and at least two assembly claws are provided, wherein the assembly claws are mounted on the support tubes in such a way that two assembly claws are provided next to each other on the support tubes, and if at least one tray is provided, which has two receptacles for the respective accommodation of a plug connection, to enable the insertion of the tray onto both of the assembly claws, this is advantageous in that the tray can be simply affixed at any desired height. Both of the assembly claws holding the tray can be mounted on both rods at any height that will fulfill the purposes of the medical arrangement on the tray. The plug connections are plugged into the receptacles of the tray. Thus, the assembly of the tray is carried out.

If the receptacles are provided between the walls, then they have a stabilizing effect on the tray.

The invention is described in detail below with reference to figures that show an exemplary embodiment. The following is shown:

FIG. 2 shows a perspective view of a tray from FIG. 1;

FIG. 3 shows a side view of the tray from FIG. 2;

Figure 1:
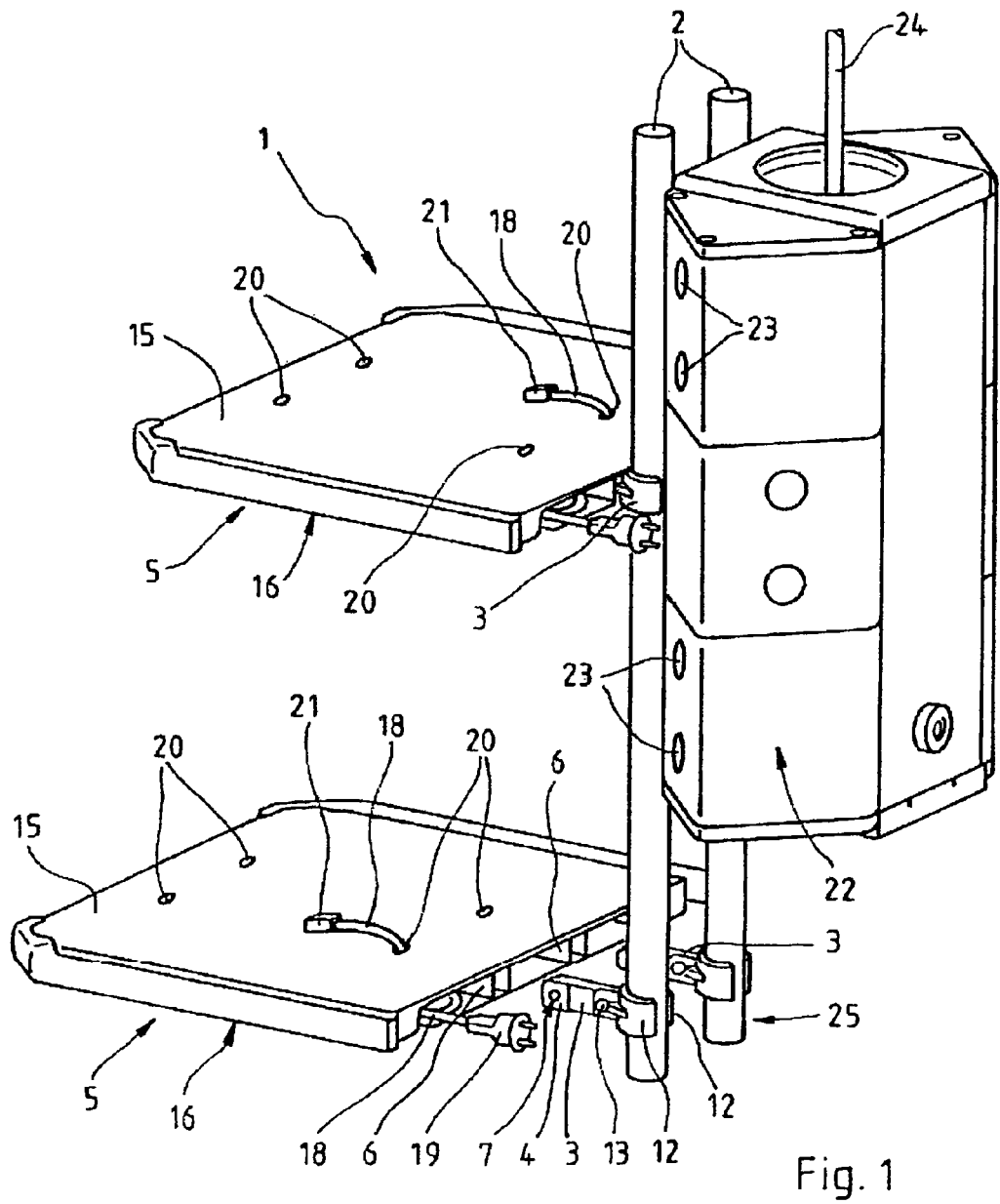
FIG. 1 shows a perspective view of the console with two vertical support tubes and two trays, each of which has storage spaces to accommodate electric cables, and which are each mounted on support tubes with two plug connections.
Figure 4:
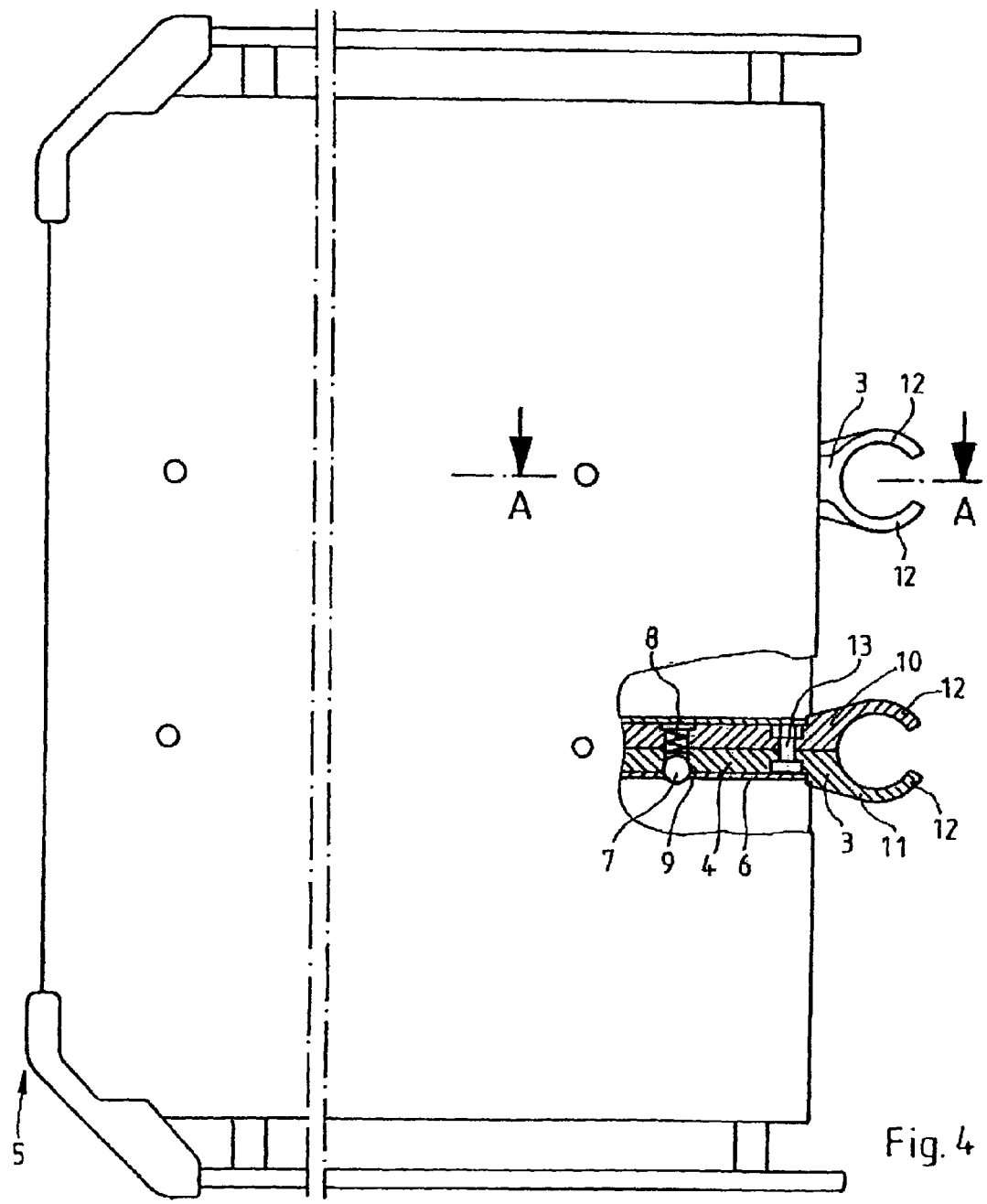
FIG. 4 shows a view from above with a partial cut-out of the tray from FIG. 2, but without the electric cable and with the plug connections inserted.
Figure 5:
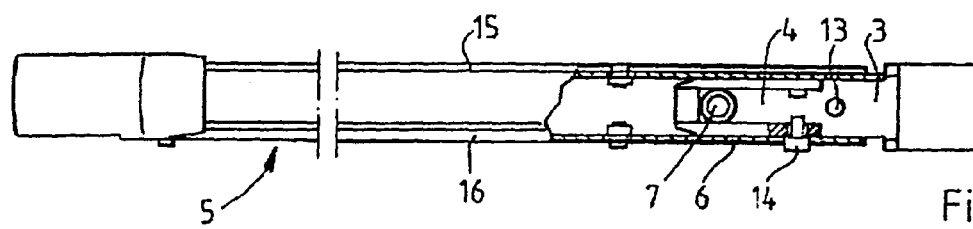
FIG. 5 shows a side view that is rotated by 90° with respect to the view in FIG. 3 with a partial cut-out of the tray from FIG. 4.

With a console 1 for the hospital sector, with two vertical support tubes 2, and with four assembly claws 3, the assembly claws 3 are mounted onto the support tubes 2 in such a way that two assembly claws 3 are provided next to each other on the supports tubes 2 in each case. Each of the assembly claws 3 has a plug connection 4. Each of the two trays have two receptacles 6 executed as a rectangular tube for the respective accommodation of a plug connection 4 to enable insertion of the tray onto the two assembly claws 3.

The plug connection 4 has a ball 7, which is held in the plug connection 4, and which is pre-loaded up against the plug connection 4 using a spring 8. The ball 7 is provided for latching into a recess 9 of the receptacle 6.

The assembly claws 3 consist of two claw parts 10,11, each of which has a gripping element 12. The claw parts 10,11 are connected to each other using a connection element 13, which is executed as a screw. A securing element 14, which is a screw, is provided for securing the plug connection 4 in the receptacle 6.

Each tray 5 has an upper wall 15 and a lower wall 16. There are two receptacles 6 and three storage spaces 17 between each of the two walls 15,16 of a tray. The storage spaces 17 are provided for accommodating electric cables 18 along with their power plugs 19. In doing so, the power plug 19 is clamped into the storage space 17. The wall distance is measured accordingly. The upper wall 15, bordering the left and the center storage space 17, has a total of four recesses 20 for individual routing of an electric cable 18, which is subsequently provided with a connector socket 21. The connector socket 21 is used to connect a medical device. A body 22 is provided on the console 1, and the body has multiple outlets 23. The outlets 23 are provided with electric current via an electric supply line 24.

1 Console
2 Support tube
3 Assembly claw
4 Plug connection
5 Tray
6 Receptacle
7 Ball
8 Spring
9 Recess
10,11 Claw part
12 Gripper element 13 Connection element
14 Securing element
15,16 Wall
17 Storage space
18 Electric cable
19 Power plug
20 Recess
21 Connector socket
22 Body
23 Outlet
24 Supply line
25 Assembly equipment The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A console for the hospital sector, comprising a support device and at least one tray, wherein the support device has at least two substantially vertical support members, and wherein each support member is provided with at least one assembly device which is configured to be slidably adjustable along the support member to be selectively mounted at a desired height on the support member and configured to mount the at least one tray cantilevered to the support device, wherein the tray has an upper wall adapted to support an item of hospital equipment thereon and a lower wall, wherein the upper wall and the lower wall of the tray define at least one storage space there-between, and the storage space is configured to accommodate a cable.

2. A console according to claim 1, wherein, in the upper wall, bordering a storage space, at least one recess is provided for routing electric cable or other cable, which preferably has a connector socket.

3. A console according to claim 1, wherein a body is provided on the console, and the body has multiple outlets, water supplies, or gas supplies, which are supplied with electrical current via an electric supply line and/or are supplied with gas or water via a supply line.

4. A console according to claim 1, wherein the assembly devices are mounted on the support members in such a way that two assembly devices are provided next to each other on the support members, wherein each of the assembly devices has a plug connection which projects from a substantially vertical plane of the support members, the plug connections of the two assembly devices extending from the support members in substantially parallel directions, and wherein the at least one tray further comprises two receptacles, each receptacle configured for the respective accommodation of one of the plug connections, to facilitate manual slidable insertion of the tray onto both of the assembly devices in said substantially parallel directions.

5. A console according to claim 4, wherein the receptacles are provided between the two walls.

6. A console according to claim 1, wherein the at least one assembly device comprises an assembly claw having claw parts which grip the respective support member.

7. A console according to claim 1, wherein the at least one tray comprises three storage spaces between the upper wall and lower wall.

8. A console according to claim 1, wherein the at least two substantially vertical support members comprise substantially vertical support tubes.

9. In a console having a support device comprising at least two substantially vertical support members, wherein each support member is provided with at least one assembly device configured to be slidably adjustable along the support member to be mounted at any desired height on the support member and configured to mount at least one tray cantilevered from the support members, the improvement comprising:
a console tray comprising: an upper wall adapted to support an item of hospital equipment thereon and a lower wall, wherein the upper wall and the lower wall of the tray define at least one storage space there-between, the storage space configured to accommodate a cable.

10. The improvement according to claim 9, wherein, in the upper wall, bordering a storage space, at least one recess is provided for routing electric cable or other cable, which preferably has a connector socket.

11. The improvement according to claim 9, wherein each of the assembly devices has a plug connection which projects from a substantially vertical plane of the support members, the plug connections of the two assembly devices extending from the support members in substantially parallel directions, and wherein the tray further comprises two receptacles for the respective accommodation of the plug connections to facilitate the manual slidable insertion of the tray onto both of the assembly devices in said substantially parallel directions.

12. The improvement according to claim 11, wherein the receptacles are provided between the upper wall and lower wall of the tray.

13. The improvement according to claim 9, wherein the console tray comprises three storage spaces between the upper wall and lower wall.

14. The improvement according to claim 9, wherein the at least two substantially vertical support members comprise substantially vertical support tubes.

* * * * *